US00PP27535P3

(12) United States Plant Patent
Zwetzig

(10) Patent No.: US PP27,535 P3
(45) Date of Patent: Jan. 10, 2017

(54) ***HIBISCUS* PLANT NAMED 'MOULIN ROUGE'**

(50) Latin Name: *Hibiscus moscheutos×H.coccineus*
Varietal Denomination: Moulin Rouge

(71) Applicant: Gretchen Angela Zwetzig, Lindsay, CA (US)

(72) Inventor: Gretchen Angela Zwetzig, Lindsay, CA (US)

( * ) Notice: Subject to any disclaimer, the term of this patent is extended or adjusted under 35 U.S.C. 154(b) by 131 days.

(21) Appl. No.: 14/121,035

(22) Filed: Jul. 23, 2014

(65) Prior Publication Data

US 2016/0029533 P1 Jan. 28, 2016

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter hardy *Hibiscus* plant named 'Moulin Rouge' is the result of a unique hybridization. This new and distinct cultivar is characterized primarily as to its novelty by its extreme cold hardiness to Zone 4, its large thick-textured, ruffled dark red flowers and its ovate to "Maple-shaped" foliage with its deep bronze coloration, compactness of approximately 2½ feet, its vigorous and uniform breaking habit and its floriferous nature from Summer until Frost.

1 Drawing Sheet

Latin name: *Hibiscus moscheutos×H. coccineus*
Varietal denomination: 'Moulin Rouge'.

FIELD OF THE INVENTION

This plant, as a hybridized hardy *Hibiscus*, is valuable to the landscape market for its improvements in thicker textured and bold red colored flowers and buds, refined, ovate to "maple-like" foliage with a bronze-purple color, its all-around vigor, stable compact breaking action, and adaptation to extreme environments, including the ability to consistently survive winter temperatures of at least −30 degrees Fahrenheit.

BACKGROUND OF THE NEW PLANT

1. The new plant of this invention is the result of a unique hybridization, with the breeding achievement being evidenced in the outstanding combination of characteristics exhibited by this new and distinct *Hibiscus* plant, which include:
(a) Refined, 3-5 lobed ovate to "maple-shaped " leaves of a bronze-purple color and relatively smooth margins which combined compliments the landscape;
(b) Medium to large-sized flowers that are outstanding for their dark red slightly ruffled petals;
(c) The plant being very floriferous with flowers that stay open for at least one to two days;
(d) The plant being small to medium-sized but vigorous with compact and uniform breaking action which gives it unique landscape utility; and
(e) The plant being so hardy that it can consistently withstand winter temperatures of at least −30 degrees Fahrenheit .

SUMMARY OF THE INVENTION

2. 'Moulin Rouge' was the result of a 68-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected 3. This new plant first bloomed in the summer of 2006 and was selected by Gretchen Zwetzig on Gretchen Zwetzig's property located at Skyline Dr. Lincoln, Nebr. (previous address for applicants,) and 267 N Strathmore Ave, Lindsay Calif. Asexual propagation of the plant by cuttings and root division in Lincoln, Nebr. and Lindsay, Calif. has shown that the unique and distinguishing features of the plant are faithfully transmitted from generation to generation and appear to be fixed.
4. Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

5. The flower and foliage of the cultivar at 2½ years of age are shown in the attached photographs. More specifically, FIG. 1 is a close-up of the flower and the leaf.
6. The colors are as true as is reasonably possible to attain in photographic illustrations of this type. The colors illustrated may be slightly off due to light reflectance.

DESCRIPTION OF THE NEW PLANT

7. What follows is a detailed description of the new cultivar. The specific color descriptions are in accordance with The Royal Horticultural Society Colour Chart (2001), while general color recitations are consistent with ordinary American terminology.

8. 'Moulin Rouge' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4) and Lindsay, Calif. (USDA Zone 9).

THE PLANT

Parentage:

*Seed parent.*—*Hibiscus moscheutos*, unnamed and unpatented Fleming-bred seedling.

*Pollen parent.*—*Hibiscus coccineus*, unnamed and unpatented Fleming-bred seedling.

Comparison between observed plant and parents: Parents were similar, except for being approximately 1 foot taller in height than Observed Plant.

Comparison between observed plant and other known cultivars: The Observed Plant is unique, but most similar to Fleming patented hardy *Hibiscus*: Robert Fleming U.S. Plant Pat. No. 14,776 and the other patented hardy *Hibiscus* from Gretchen Zwetzig, in that.

(*a*).—they are all more compact at 3 feet on average.

(*b*).—they are all more hardy to −30 degrees Fahrenheit.

(*c*).—they all have refined new leaf shapes and colors.

(*d*).—they all have thick, overlapping new flower colors with blooms from the top to the bottom of the plant. New plant is different from Robert Fleming with the addition of the copper-purple leaf coloration.

Origin: A selected seedling from stated cross.

Type of plant: Hardy, herbaceous perennial.

Classification: Variety of hardy *Hibiscus* plant.

Propagation: Relatively easy to propagate through cuttings; holds its distinguishing characteristics through successive cuttings and divisions.

Size: About 2½ to 3 feet tall and about 2½ feet wide.

Form: Symmetrical annual growth from perennial roots.

Habit: Upright and uniformly branched.

Growth: Vigorous; medium and compact. Full grown (2½ to 3 ft) within 2 years. 2 ft 5 inches at the time of measurement.

Hardiness: Hardy to at least −30 degrees Fahrenheit.

General health: Plant is very disease resistant against rot, aphids, spider mites, scale, white fly etc.; sturdy through excessive drought, rain or wind.

Propagation: Relatively easy and fast rooting in approximately 2 weeks.

Foliage:

1. *Arrangement*.—Alternate.
2. *Shape*.—Juvenile: 3-5 lobed ovate to "maple-shaped" leaves. Rounded base shape. Mature: Refined, ovate to "maple-shaped", 3-5 lobed leaf with entire to mildly serrate margins and acute apices; rounded base.
3. *Size*.—Mature leaf (petiole base to apex): Length is about 5 inches, width is about 3 inches. Young leaf: Length 3¾ inches, width is 2½ inches.
4. *Color*.—Young leaves (upper side): 147-A; (purple color): N 92-A and 187-A. Mature leaves: (upper side): 147-A. A blend of 187-A and 178-A. Veins: 185-A. Venation pattern (Young and Old): Palmate. Venation Color: 185-A.

Coloration of the lower leaf surface: Between 137 and 139 C.

5. *Surface texture*.—Upper: Smooth. Lower: Semi-smooth.
6. *Petiole length*.—About 2¾ inches or 6.5 cm. Diameter: 1-2 cm.
7. *Petiole color*.—137-A and 178-A. Petiole texture: Semi-smooth.

Stems: The stems are stout at the base becoming more slender toward the apices; coloration is consistent with the petiole.

Length: 2-3 inches. Diameter: 1-2 cm.

Internode length: Apx. 2 inches.

Texture: Semi-smooth.

THE FLOWER

Blooming period: Profuse from June/July until frost depending on location of either South/North US.

Flower diameter: Large; about 9-10 inches.

Borne: Singly in leaf axils, from midpoint of stems upward.

Bloom duration: Individual bloom lasts at least one to two full days.

Form: Campanulate; petals are also very overlapping.

Average number of flowers per season: 300.

Bud:

1. *Length*.—About 2¼ inches on day before opening. Diameter: apx. 2 inches.
2. *Color*.—Darker than N77.
3. *Surface texture*.—Semi-glabrous.
4. *Duration*.—One to two weeks.

Corolla: Having five petals.

1. *Petal character and dimensions*.—Campanulate and very overlapping. (a) Young Length: About 3¾ inches. Mature Length: About 5 inches. (b) Young Width: About 2½ inches. Mature Width: About 3 inches.
2. *Coloration of upper and lower petal surface*.—Dark Red. Between 53A and 59A. (a) Venation: 59-A. (b) Eye zone: 59-A. Size: 2½ inches.
3. *Texture*.—Smooth.
4. *Substance*.—Thick.
5. *Shape*.—Campanulate and very overlapping with petal ruffles at edges.

Reproductive organs:

1. *Staminal column*.—Stamen along basal two-thirds. Average number per flower: 1. Staminal column average length: About 1¾ inches. Staminal column average color: Lighter than 11-D. Pollen color: 11-C and B.
2. *Style*.—Terminates upper one-third of stamina column. Average Length: ½ to ¾ inch. Color: 11-D. Stigmatic lobe color: 11-D (tips: 63-A). Stigma average size: 1/16 inch.

Calyx: Connate at the base; about 1¼ inches or (3.5 cm) in length.

*Color*.—Medium green: 147-A.

Stipules: None.

Seed (fruit):

*Size*.—1 cm.

*Color*.—Grey-brown (RHS 166 B).

*Average number*.—Less than 100.

Epicalyx: Whorl of bracts.

1. *Shape*.—10-12 slender, sword-shaped bractlets.
2. *Length*.—About 1½ inches or (3.8 cm).
3. *Color*.—143-A.

Peduncle:

1. *Length*.—About 2 inches or (6½ cm). Diameter: 1 cm.
2. *Strength*.—Stiff and sturdy.
3. *Color*.—Light to medium green with slight reddish-purple cast. 148-A and 175 A.
4. *Surface texture*.—Semi-smooth.

The invention claimed is:

1. A new and distinct cultivar of hardy *Hibiscus* plant, as herein shown and described, characterized by its compact nature, refined ovate to "maple-shaped" foliage of a deep bronze-purple coloration, its large dark red flowers, its vigor and its hardiness.

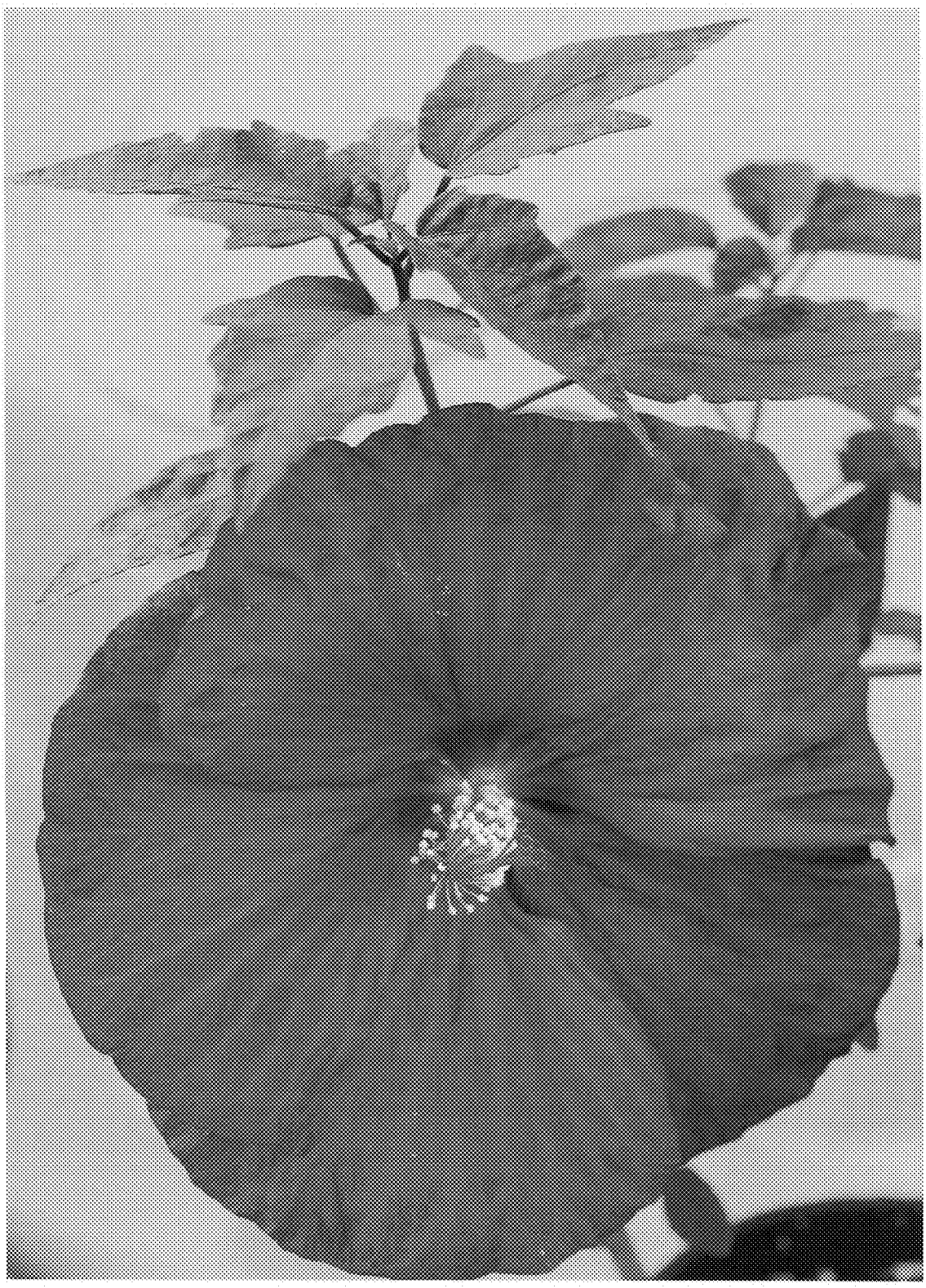

* * * * *